May 24, 1949. R. L. BYRUM Plant Pat. 838
ROSE PLANT
Filed Sept. 19, 1947
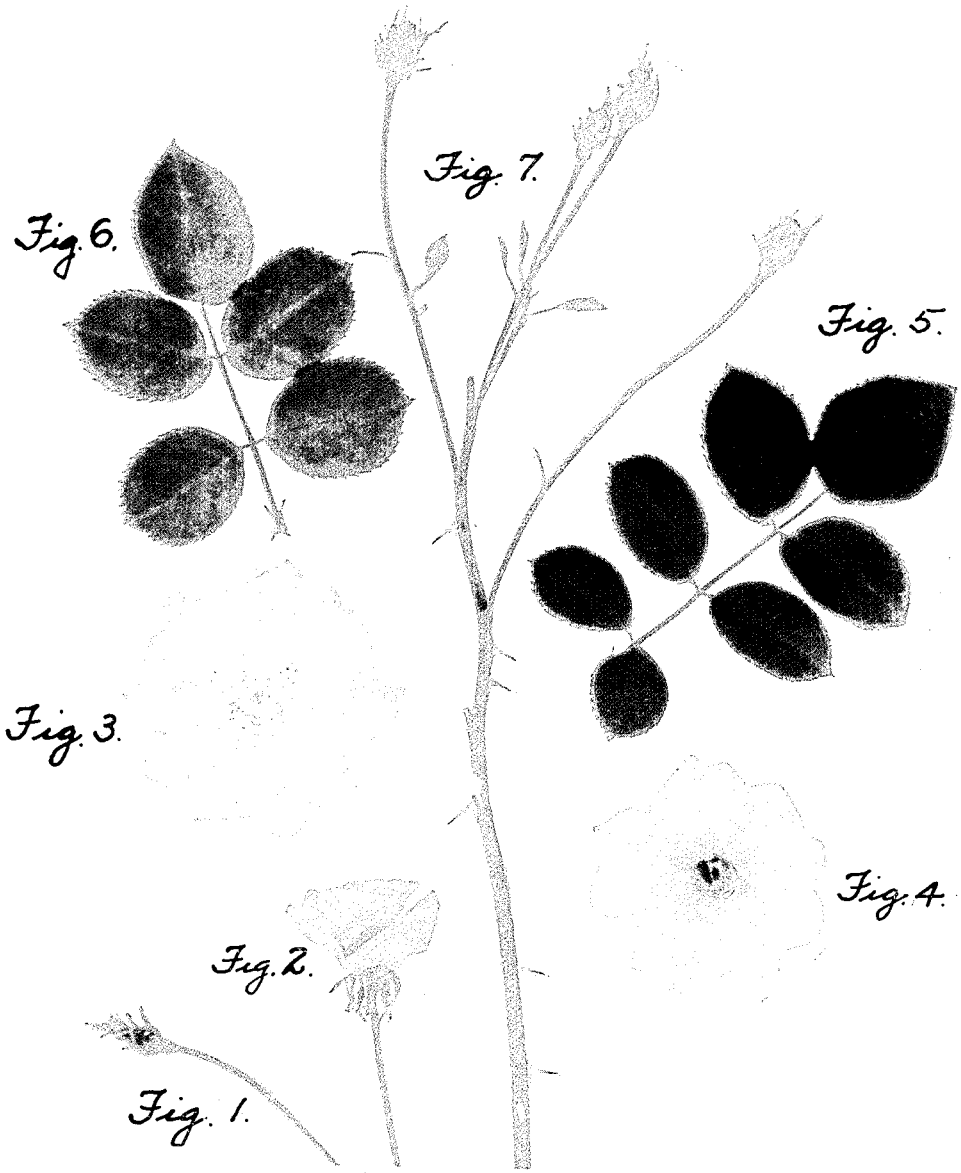
Inventor:
Roy L. Byrum
By: Robert Robb
Attorneys.

Patented May 24, 1949

Plant Pat. 838

UNITED STATES PATENT OFFICE

838

ROSE PLANT

Roy L. Byrum, Richmond, Ind., assignor to Joseph H. Hill Company, Richmond, Ind., a corporation of Indiana Application September 19, 1947, Serial No. 774,915

1 Claim. (Cl. 47—61)

The present invention relates to a new and distinct variety of rose plant of the polyantha class, resulting from the crossing of the "Juanita" and "Mrs. R. M. Finch" varieties.

The distinctive characteristics of this new rose may best be understood by comparing it with the well-known polyantha variety "Betty Prior" (Pl. Pat. #340) which it more nearly approaches than any other varieties of this group. Dominantly, the present rose variety, in this comparison, grows much heavier canes, differs as to its thorns, and the flower is slightly larger and of entirely different color, all as hereinafter more specifically disclosed.

Asexual reproduction of this new variety shows the foregoing characteristics come true to form and are established.

In the drawing:

Figure 1 is a view of the bud of this new variety, before the calyx breaks, showing its small size and the foliaceous appendages;

Figure 2 is a view of the bud as the petals begin to open;

Figure 3 is a top view of a specimen of the full blown flower, showing its distinctive color and petal arrangement;

Figure 4 shows the reverse side of the bloom and the difference in color of the under reverse as compared with the upper surface;

Figure 5 is a top view of the specimen of the foliage, showing the compound of seven leaflets;

Figure 6 is a reverse view of a specimen of the foliage, showing the compound of five leaflets; and Figure 7 is a view of a specimen of a main stem, showing the cluster arrangement of blooms and the particular characteristics of the distinct thorns.

The following is a detailed description of the new variety, color terminology being in accordance with Ridgway's Color Standard, except where otherwise indicated to have ordinary dictionary significance:

Type: Hardy; bush; outdoor; seedling; for garden decoration.

Class: Polyantha.

Breeding: Seedling.

*Seed parent.*—"Juanita" (unpatented).

*Pollen parent.*—"Mrs. R. M. Finch" (unpatented).

Propagation: Holds its distinguishing characteristics through succeeding propagations by cutting, grafting, and budding.

Locality where grown: Richmond, Indiana.

Flowers borne: Three to several to stem in irregular clusters on normal, medium-length stems.

Quantity of bloom: Abundant, outdoors and in greenhouse.

Continuity: Continuous.

Fragrance: Slight; tea.

Bud:

*Peduncle.*—Short; medium heavy; erect; light green; numerous prickles.

*Before calyx breaks.*—*Size*—small. *Form*—short; flat; ovoid with a conspicuous neck; with foliaceous appendages on the surface of the bud; with much cut foliaceous parts extending beyond the tip of the bud equal to one-half or more of its length.

*As calyx breaks.*—*Color*—Spinel Red, Plate XXVI.

*As first petal opens.*—*Size*—very small. *Form*—short; flat; ovoid. *Color*—outside: Spinel Red, Plate XXVI; inside: Spinel pink, Plate XXVI.

*Opening.*—Opens up well.

Bloom: Size, when fully open—small; 1″ to 2″.

*Petalage.*—Single; from five to six petals arranged regularly.

*Form.*—Flat; open; petals at first loosely flat rolled outward; remaining later, at maturity, rolled outward and flat.

Petals: Thick; inside and outside satiny.

*Shape.*—Outside—obovate with one notch. Inside—obovate with one notch.

This description of a newly opened flower was made from a rose grown outdoors in the month of June, at Richmond, Indiana:

*Color.*—*Outside petal*—outside surface: Spinel Pink, Plate XXVI; inside surface: Thulite Pink, lightly pencilled with Spinel Pink, Plate XXVI. *Inside petal*—outside surface: Spinel Pink, Plate XXVI; inside surface: Thulite Pink, pencilled with Spinel Pink.

This description was made from a rose that was open for three days outdoors in the month of June, at Richmond, Indiana:

*Color.*—*Outside petal*—outside surface: Thulite Pink, shading to white at base of petals; inside surface: Cameo Pink, pencilled with Thulite Pink, both Plate XXVI. *Inside petal*—outside surface: Thulite Pink, shading to white at base of petals; inside surface: Cameo Pink, pencilled with Thulite Pink.

*General color effect.*—Newly opened flower—Spinel Pink. Three days open—Thulite Pink.

*Behavior.*—Persist.

*Flower longevity.*—On bush in garden—five or more days in June. Cut roses grown outdoors kept at living-room temperatures—four to five days in June.

*Reproductive organs*

Stamens: Many; arranged irregularly about pistils.

Filaments: Medium length; yellow; most with anthers.

Anthers: Small; yellow; all open at once.

Pollen: Abundant; gold.

Pistils: Medium number.

Styles: Even; short; medium heavy; bunched.

Stigma: White.

Ovaries: All enclosed in calyx.

Sepals: Permanent; moderately short; spear-shaped. *Color*—inside: Turtle Green, Plate XXVII; outside: Chromium Green, Plate XXVII.

*Plant*

Foliage:

*Leaves.*—Compound of five to seven leaflets; very abundant; medium large; leathery.

*Leaflets.*—Shape, ovoid with apex obtuse; base obtuse; margin simply serrate.

*Color.*—*Mature*—upper surface: dark green; under surface: moderately green. *Young*—upper surface: bronze red; under surface: bronze red.

*Rachis.*—Medium heavy. Upper side—grooved; under side—sparsely thorny.

*Stipules.*—Very short; very narrow; with short points turning out at an angle of less than 45°.

*Disease.*—Resistant to mildew and blackspot.

Growth:

*Habit.*—Bush; upright; much branched.

*Growth.*—Vigorous.

*Canes.*—Medium heavy.

*Main stem.*—Green. *Thorns*—many; long; hooked downward; with short, narrow base. *Prickles*—none. *Hairs*—none.

*Branches.*—Bright green. *Thorns*—many; long; hooked downward; with short, narrow base. *Prickles*—none. *Hairs*—none.

*New shoots.*—Bronze red. *Thorns*—many; long; hooked downward; with short, round base. *Prickles*—none. *Hairs*—none.

It will now be apparent that this new variety resembles its seed parent in color and in the fact that its bloom is single. However, it is not as free a bloomer as "Juanita" and its grows more in clusters than the latter. The new rose resembles its pollent parent as regards the cluster growth, but said parent has more petals and is a lighter pink. The petals of "Mrs. R. M. Finch" are the same in color on top and bottom, while those of this new variety are dark on the bottom and light on top. Actually, the purpose of making this cross was to improve upon the "Mrs. R. M. Finch" variety in respect to the flower and this objective was accomplished.

I claim:

A new and distinct variety of rose plant of the polyantha class, characterized as to novelty by its heavy canes, the form and color of its thorns, and by the size and color of its blossoms, substantially as shown and described.

ROY L. BYRUM.

No references cited.